(12) United States Patent
Ross

(10) Patent No.: US 9,968,475 B2
(45) Date of Patent: May 15, 2018

(54) ALTERNATING COMPRESSION PELVIC TRAUMA BINDER

(71) Applicant: Matthew S. Ross, Harrisburg, PA (US)

(72) Inventor: Matthew S. Ross, Harrisburg, PA (US)

( * ) Notice: Subject to any disclaimer, the term of this patent is extended or adjusted under 35 U.S.C. 154(b) by 213 days.

(21) Appl. No.: 14/710,527

(22) Filed: May 12, 2015

(65) Prior Publication Data

US 2015/0359541 A1 Dec. 17, 2015

Related U.S. Application Data

(60) Provisional application No. 61/991,932, filed on May 12, 2014.

(51) Int. Cl.
| | |
|---|---|
| *A61B 17/135* | (2006.01) |
| *A61F 5/34* | (2006.01) |
| *A61F 5/058* | (2006.01) |
| *A61F 13/14* | (2006.01) |
| *A61H 9/00* | (2006.01) |

(52) U.S. Cl.
CPC ............ *A61F 5/34* (2013.01); *A61F 5/05816* (2013.01); *A61F 13/148* (2013.01); *A61H 9/0078* (2013.01); *A61H 2201/165* (2013.01); *A61H 2201/1628* (2013.01)

(58) Field of Classification Search
CPC ..... A61H 9/0078; A61F 5/05816; A61F 5/34; A61F 13/148

USPC ......................................................... 606/203
See application file for complete search history.

(56) References Cited

U.S. PATENT DOCUMENTS

| | | | |
|---|---|---|---|
| 6,852,089 B2 * | 2/2005 | Kloecker | ................. A61F 5/34 128/878 |
| 8,192,383 B2 | 6/2012 | Polliack et al. | |
| 8,926,536 B2 * | 1/2015 | Hopman | ............. A61B 17/135 602/13 |

* cited by examiner

*Primary Examiner* — Vy Bui
(74) *Attorney, Agent, or Firm* — Baker Hostetler LLP

(57) ABSTRACT

The present disclosure is generally directed to systems, devices, and methods for compressing the pelvis with alternating compressive air compartments by encircling the hip region of the patient. In some examples, a device may be applied to a person with a traumatic pelvic injury. A main body may include a strong flexible material such as neoprene and may have the general shape of a wide belt or pelvic girdle. The interior or exterior aspect of the binder may be composed of one or many straps that extend from one end of the binder and are looped through buckles on the other end of the binder and may therefore allow for tightening of the binder upon itself for compression. The end of the strap may contain a fastening device to affix the end of the strap to itself after the strap has been looped through the buckle.

5 Claims, 3 Drawing Sheets

ALTERNATING COMPRESSION PELVIC TRAUMA BINDER

CROSS-REFERENCE TO RELATED APPLICATIONS

This application claims priority to and the benefit of U.S. Provisional Application No. 61/991,932, entitled "ALTERNATING COMPRESSION PELVIC TRAUMA BINDER," filed on May 12, 2014, the disclosure of which is incorporated herein by reference.

TECHNICAL FIELD

The disclosure is generally directed to a medical device and methods used for the compression of a human pelvis.

BACKGROUND

Compressive binder devices for severely traumatized pelvic injuries are a well-known treatment in the medical arts. Severe pelvic ring injuries can damage venous and arterial vasculature as well as pelvic and abdominal viscera. Pelvic ring injuries have been shown to have an associated mortality rate of between 10%-50% depending on the severity of the energy imparted to the pelvis. Rapid exsanguination can occur in severe injuries that damage the pelvic vasculature, aggressive management of this hemorrhage with compression has proven to be the optimal initial treatment.

The pelvic binder or sheet is now the standard of care for the initial treatment of most exsanguinating pelvic ring injuries. Some purposes of the binder or sheet are to:
1. Apply a significant amount of constant force to the pelvis in order to reduce the pelvic volume;
2. Splint the bony pelvis to reduce hemorrhage from fractured bone ends and venous disruption;
3. Stabilize and maintain the integrity of the pelvis for future definitive surgical treatment; and/or
4. Reduce pain.

Conventionally, the binder is applied in a uniform manner that applies pressure on the lateral aspects of the greater trochanters of the hips proximal femurs, so as to compress the hips from the lateral aspect medially. The binder must be applied in a uniform manner so as to distribute the compressive force over a wide surface area on the lateral hips. The uneven distribution of this compressive force has led to the development of pressure induced skin and soft tissue breakdown and necrosis. This soft tissue breakdown and necrosis has been shown to significantly increase the morbidity and mortality of the traumatized patient.

Even with uniform application of a pelvic binder or sheet there is still significant compressive force applied to the pelvis. Skin breakdown and necrosis over bony prominences is still a major complication with the long-term use of a properly applied binder or sheet. Many orthopedic surgeons will elect to remove the pelvic binder after 24 hours and surgically apply an external fixator device in its stead to avoid skin breakdown complications The surgical application of an external fixator device is not without major possible complications as the patient is often in a critical state of health and even minor insults such as anesthesia or mobilization can quickly cause the patient's status to deteriorate. In many cases the patients' health is in such a precarious state that longer term application of the pelvic binder would allow for the stabilization of their overall health status before they go to surgery for either the application of an external fixator or a more definitive surgery.

DESCRIPTION OF DRAWINGS

The foregoing and other features of the present disclosure will become more fully apparent from the attached drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1:
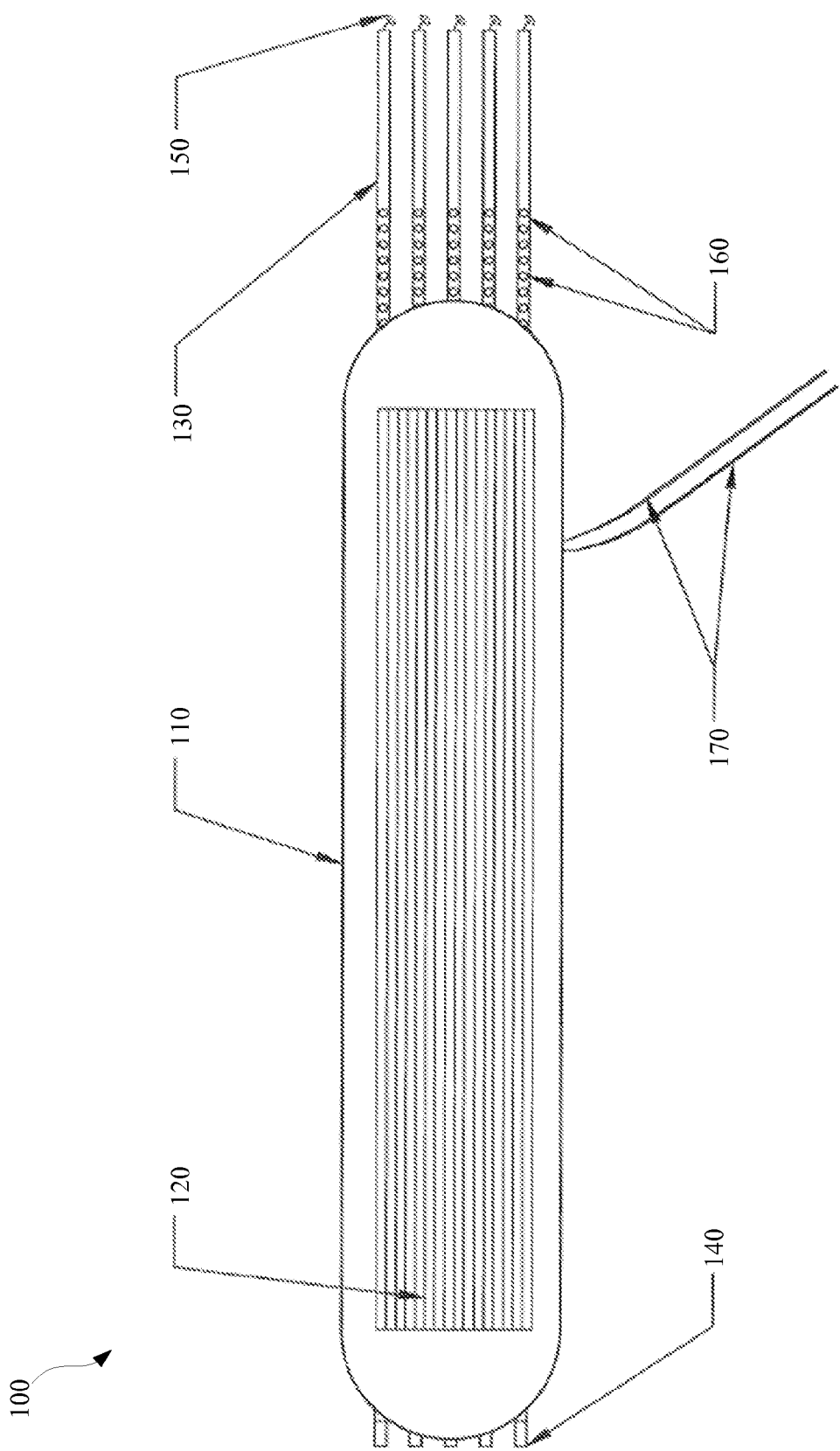
FIG. 1 provides an internal, elevational view of an example binder in accordance with at least an embodiment of the present disclosure.

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented here. It will be readily understood that the aspects of the present disclosure, as generally described herein, and illustrated in the Figures, may be arranged, substituted, combined, and designed in a wide variety of different configurations, all of which are explicitly contemplated and make part of the present disclosure.

Figure 2:
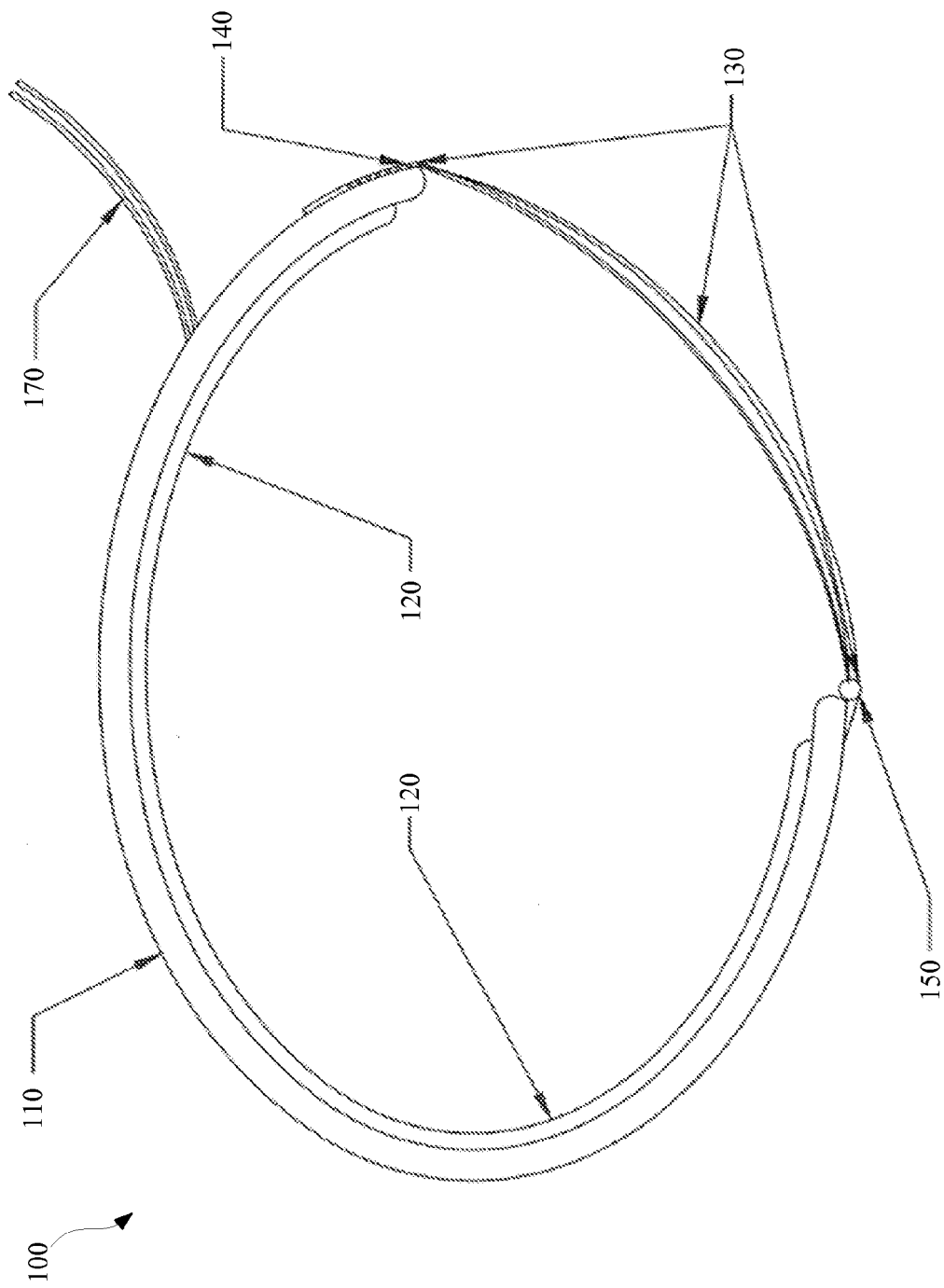
FIG. 2 provides a top view of the exemplary binder of FIG. 1.
Figure 3:
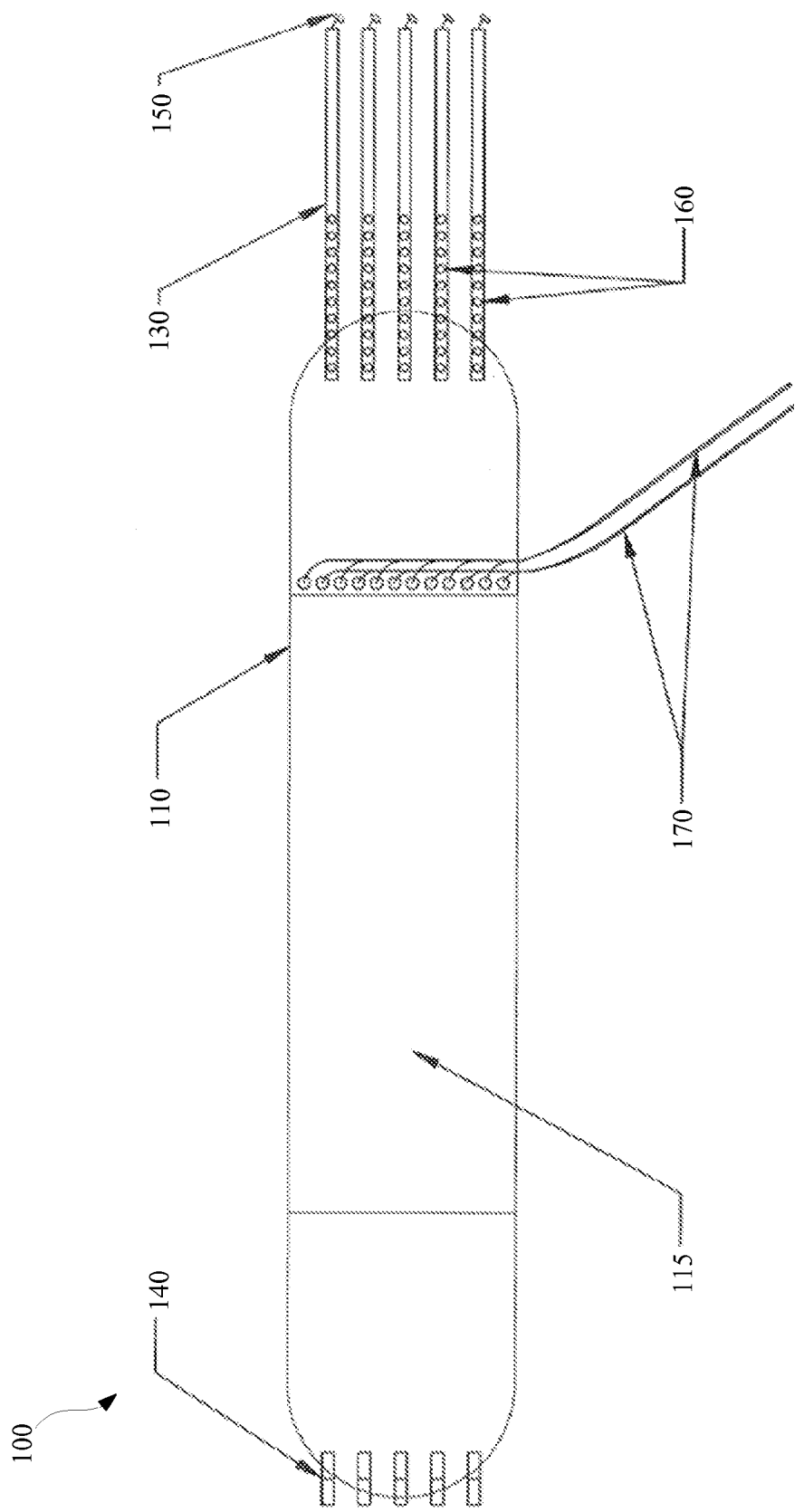
FIG. 3 provides an external, elevational view of the exemplary binder of FIGS. 1 and 2, all arranged in accordance with at least an embodiment of the present disclosure.

As shown in FIGS. 1-3, examples of the present disclosure are directed to a device and methods for using such a device that may be applied, as a means of pelvic compression, to a severely traumatized patient with a pelvic ring injury for prolonged periods of time avoiding the major complication of skin breakdown. Example of the present disclosure may include a binder device 100 having a body 110 composed of material that allows for compression of the bony pelvis. The inner aspect of the body 100 may have inflatable pressurized compartments 120 arranged in small rings (as shown in FIG. 2) of variable diameters, for example, that can be pressurized and/or de-pressurized to variable pressure settings by a pressurization system.

Example pressurization systems may be set to pressurize alternate compartments 120 of the binder device 100 at any one time. The alternate compartments 120 when not pressurized may be deflated and apply no significant pressure to the pelvis. At time intervals (e.g., variable time intervals), the deflated compartments 120 may be pressurized and inflate to the same pressure as the alternating compartments 120 then those alternating compartments 120 may deflate, relieving the pressure on the skin and soft tissue under those compartments 120.

This alternating pressurization system may allow for the skin and soft tissue that is being directly compressed by the pressurized compartments 120 of the binder device 100 to have a set time of depressurization while its adjacent compartments 120 are pressurized and maintaining the compressive force on the bony pelvis. This process may allow for blood flow to the soft tissues and skin for a set period of time before the alternate compartments 120 are compressed again and that compartment 120 becomes pressurized. This process allows the binder to maintain the compression needed to inhibit intra pelvic bleeding while maintaining the necessary blood flow to the skin and soft tissues in order to inhibit the major complication of skin breakdown and necrosis.

The present disclosure is generally directed to systems, devices, and methods for compressing the pelvis with alternating compressive air compartments 120 by encircling the hip region of the patient. In some examples, a device 100 may be applied to a person with a traumatic pelvic injury. A main body portion 110 may be composed of a strong flexible material such as neoprene and may have the general shape of a wide belt or pelvic girdle. The interior or exterior aspect 115 of the binder 100 may be composed of one or many strap apparatuses (or strap) 130 that extend from one end of the binder 100 and are looped through buckles 140 on the other end of the binder and may therefore allow for tightening of the binder 100 upon itself for compression. The end of the strap 130 may contain a fastening device 150 to affix the end of the strap 130 to itself after the strap 130 has been looped through the buckle 140. The strap 130 may have many fastener receptacles 160 on its proximal aspect allowing for different mating sites for the fastening device 150. In some examples, the fastening receptacles 160 may be evenly spaced. The fastening receptacles 160 may be placed at variable increments. These different mating sites allow for adjustable tensioning forces to be applied to the pelvis. It is within the scope of the current disclosure to utilize any appropriate fastener 150 as may be known to those of ordinary skill such as, for example: buckles, belts, ties, hook and loop (such as Velcro®) and the like.

The main body 110 of the binder 100 may be composed of a flexible yet non-stretchable material such as neoprene that allows for a conforming fit to the individual patient yet does not allow for stretching of the material and subsequent loss of compression over time. The exterior aspect 115 of the binder 100, excluding the strap apparatus 130, may be covered with a low friction material so as to allow for easy maneuverability of the patient while in the supine position. The inner aspect of the binder 100 may be covered with a soft cushioning material that allows for even distribution of forces to the patient's body's surface area.

The inner aspect of the main body 110 of the binder 100 may house multiple inflatable air chambers 120 that may be of variable diameters when fully inflated. These chambers 120 may be arranged in multiple different orientations including horizontal, vertical, or at an angle to the main body 110. The chambers 120 may be constructed such that when fully inflated they may cause pressure upon the patients' hips and subsequent cause pelvic compression. The chambers 120, when deflated, may put lesser or no pressure on the hips if the alternating chamber 120 is inflated and causing compression. In some examples, the chambers 120 may be inflated in an alternating pattern so that every other chamber 120 at any one time may be inflated and causing pressure on the pelvis.

The chambers 120 may be made of an airtight material that is housed directly next to the inner body material. This may allow for the chambers 120 to exert pressure on the hips while not exposing the skin to an abrasive surface area. The cushioning aspect of the inner body material may shield the body from abrasion and ulceration over time while still allowing for pelvic compression. Each chamber 120 of the binder 100 may have a pressurization hose(s) 170 coupled to the chamber 120 and coupling the chamber 120 to the external environment. This hose 170 may be used to inflate and/or deflate the chamber 120. In some examples, the hoses 170 from the multiple chambers 120 may all exit the binder 100 at one location and alternating hoses 170 may be grouped together so that alternate hoses 170 could be inflated simultaneously.

In some examples, the pressurization and depressurization of the binders' chambers 120 may be controlled by an external pressurization device that may be programmed to inflate the alternating chambers 120 at set or pre-determined time periods. The binders' hoses 170 may be of variable lengths and may be coupled to the pressurization device. The pressurization device may be used to set differing levels of compression pressure to the hips.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for compressing a pelvis comprising:
donning a compression device about a patient's pelvis, the compression device including
an elongated flexible body having an internal surface and an external surface and opposing first and second ends adapted to be worn about a patient's pelvis,
a plurality of inflatable air chambers operatively coupled to the elongated body and extending at least partially from the internal surface, and
a fastener for releasably coupling the first and the second end; and
inflating and deflating the inflatable air chambers about the patient's pelvis in a predetermined timing pattern to provide alternating compression by the inflatable air chambers;
wherein the plurality of inflatable air chambers extend substantially in parallel longitudinally along the flexible body; and
wherein the step of inflating and deflating the inflatable air chambers about the patient's pelvis in a predetermined timing pattern, (a) inflates a first set of inflatable chambers comprising every other substantially parallel inflatable chamber while simultaneously deflating a second set of chambers comprising inflatable chambers immediately adjacent to the first set and then (b) deflates the first set of inflatable chambers while simultaneously inflating the second set, wherein steps (a) and (b) are repeated according to a predetermined timing cycle.

2. A method for compressing a pelvis comprising:
donning a compression device about a patient's pelvis, the compression device including
an elongated flexible body having an internal surface and an external surface and opposing first and second ends adapted to be worn about a patient's pelvis,
a plurality of inflatable air chambers operatively coupled to the elongated body and extending at least partially from the internal surface, and
a fastener for releasably coupling the first and the second end; and
inflating and deflating the inflatable air chambers about the patient's pelvis in a predetermined timing pattern to provide alternating compression by the inflatable air chambers;

wherein the step of inflating and deflating the inflatable air chambers about the patient's pelvis in a predetermined timing pattern, (a) inflates a first set of inflatable chambers comprising every other inflatable chamber while simultaneously deflating a second set of chambers comprising inflatable chambers immediately adjacent to the first set and then (b) deflates the first set of inflatable chambers while simultaneously inflating the second set, wherein steps (a) and (b) are repeated according to a predetermined timing cycle.

3. A method for compressing a pelvis comprising:

providing a compression device designed to be donned on a patient around the patient's pelvis, the compression device including:
- an elongated flexible body having an internal surface and an external surface and opposing first and second ends adapted to be worn about a pelvis,
- a plurality of inflatable air chambers operatively coupled to the elongated body and extending at least partially from the internal surface, and
- a fastener that releasably couples the first and the second ends; and while the compression device is donned around the patient's pelvis, alternately inflating and deflating the inflatable air chambers to provide alternating compression by the inflatable air chambers on the patient's pelvis;

wherein the step of alternately inflating and deflating the inflatable air chambers includes the following:
(a) initially inflating every inflatable air chamber around the pelvis after the compression device is provided around the patient's pelvis;
(b) deflating every third inflatable air chamber;
(c) re-inflating the deflated inflatable air chambers;
(d) deflating half of the inflatable air chambers that were not deflated in step (b);
(e) re-inflating the deflated inflatable air chambers;
(f) deflating the remaining third of the inflatable air chambers that were not deflated in steps (b) or (d);
(g) re-inflating the deflated inflatable air chambers; and
(f) repeating steps (b) through (g) to provide alternating compressing by the inflatable air chambers on the pelvis.

4. A method for compressing a pelvis comprising:

providing a compression device designed to be donned on a patient around the patient's pelvis, the compression device including:
- an elongated flexible body having an internal surface and an external surface and opposing first and second ends adapted to be worn about a pelvis,
- a plurality of inflatable air chambers operatively coupled to the elongated body and extending at least partially from the internal surface, and
- a fastener that releasably couples the first and the second ends; and while the compression device is donned around the patient's pelvis, alternately inflating and deflating the inflatable air chambers to provide alternating compression by the inflatable air chambers on the patient's pelvis;

wherein the step of alternately inflating and deflating the inflatable air chambers includes the following:
(a) initially inflating every inflatable air chamber around the pelvis after the compression device is provided around the patient's pelvis;
(b) deflating every other inflatable air chamber;
(c) re-inflating the deflated inflatable air chambers;
(d) deflating the inflatable air chambers that were not deflated in step (b);
(e) re-inflating the deflated inflatable air chambers; and
(f) repeating steps (b) through (e) to provide alternating compressing by the inflatable air chambers on the pelvis.

5. The method of claim 4, wherein the plurality of inflatable air chambers extend substantially in parallel longitudinally along the flexible body.

* * * * *